(12) United States Patent
Lamm et al.

(10) Patent No.: US 12,004,786 B2
(45) Date of Patent: *Jun. 11, 2024

(54) BUNION CORRECTION SYSTEM AND METHOD

(71) Applicant: CROSSROADS EXTREMITY SYSTEMS, LLC, Memphis, TN (US)

(72) Inventors: Bradley Lamm, North Palm Beach, FL (US); Michael Chad Hollis, Collierville, TN (US); Daniel Sayger, Southaven, MS (US)

(73) Assignee: Crossroads Extremity Systems, LLC, Memphis, TN (US)

( * ) Notice: Subject to any disclaimer, the term of this patent is extended or adjusted under 35 U.S.C. 154(b) by 1048 days.

This patent is subject to a terminal disclaimer.

(21) Appl. No.: 16/859,531

(22) Filed: Apr. 27, 2020

(65) Prior Publication Data

US 2020/0253650 A1 Aug. 13, 2020

Related U.S. Application Data

(63) Continuation of application No. 16/033,086, filed on Jul. 11, 2018, now Pat. No. 10,646,263.

(51) Int. Cl.
*A61B 17/72* (2006.01)
*A61B 17/16* (2006.01)
(Continued)

(52) U.S. Cl.
CPC ...... *A61B 17/7291* (2013.01); *A61B 17/1682* (2013.01); *A61B 17/1717* (2013.01);
(Continued)

(58) Field of Classification Search
CPC ............ A61B 17/7291; A61B 17/1775; A61B 17/1682; A61B 17/1717; A61B 17/7233;
(Continued)

(56) References Cited

U.S. PATENT DOCUMENTS 5,449,360 A * 9/1995 Schreiber ............. A61B 17/152
606/87
H1706 H * 1/1998 Mason ............................ 606/87
(Continued)

FOREIGN PATENT DOCUMENTS

| DE | 202005012942 | 12/2005 |
|----|----|----|
| EP | 2228026 | 11/2013 |
| FR | 2878431 | 6/2007 |

*Primary Examiner* — Lynnsy M Summitt
(74) *Attorney, Agent, or Firm* — BakerHostetler

(57) ABSTRACT

A minimally invasive method of correcting a bunion includes performing an osteotomy to divide the metatarsal into first and second portions, implanting a nail in the first portion, securing a suture to the joint capsule, tensioning the suture to align the great toe with the metatarsal, attaching the suture to the nail, and fastening the nail to the second portion. A first guide block includes a plurality of coplanar passages to guide an instrument to create one or more holes in the metatarsal in advance of the osteotomy, and a second guide block includes a guide slot for another instrument to complete the osteotomy. The method can be performed through an incision of 0.5 inches or less. The nail includes an anchor portion for anchoring in the first portion, a head for attachment to a second portion, and can include a passage for attachment of the suture.

19 Claims, 10 Drawing Sheets

(51) Int. Cl.
*A61B 17/17* (2006.01)
*A61B 17/80* (2006.01)
*A61B 17/84* (2006.01)
*A61B 17/56* (2006.01)

(52) U.S. Cl.
CPC ...... *A61B 17/1775* (2016.11); *A61B 17/7233* (2013.01); *A61B 17/8061* (2013.01); *A61B 17/848* (2013.01); *A61B 2017/565* (2013.01)

(58) Field of Classification Search
CPC .. A61B 17/8061; A61B 17/848; A61B 17/151
See application file for complete search history.

(56) References Cited

U.S. PATENT DOCUMENTS

| | | | | |
|---|---|---|---|---|
| 5,810,822 | A * | 9/1998 | Mortier | A61B 17/809 606/101 |
| 5,843,085 | A * | 12/1998 | Graser | A61B 17/15 606/87 |
| 6,007,580 | A * | 12/1999 | Lehto | A61F 2/4225 623/18.11 |
| 6,203,545 | B1 * | 3/2001 | Stoffella | A61B 17/68 606/74 |
| 6,248,109 | B1 * | 6/2001 | Stoffella | A61B 17/68 606/62 |
| 6,576,018 | B1 * | 6/2003 | Holt | A61B 17/68 606/328 |
| 6,689,136 | B2 * | 2/2004 | Stoffella | A61B 17/68 606/328 |
| 7,572,258 | B2 * | 8/2009 | Stiernborg | A61B 17/152 606/79 |
| 7,901,431 | B2 * | 3/2011 | Shurnas | A61B 17/683 606/232 |
| 7,909,880 | B1 * | 3/2011 | Grant | A61F 2/4225 623/21.19 |
| 8,277,459 | B2 * | 10/2012 | Sand | A61B 17/1682 606/86 R |
| 8,282,645 | B2 * | 10/2012 | Lawrence | A61B 17/15 623/21.19 |
| 8,303,589 | B2 * | 11/2012 | Tyber | A61B 17/864 606/301 |
| 8,313,487 | B2 * | 11/2012 | Tyber | A61B 17/1775 606/62 |
| 8,328,806 | B2 * | 12/2012 | Tyber | A61B 17/72 606/62 |
| 8,343,152 | B2 | 1/2013 | Gonzalez-Hernandez | |
| 8,343,199 | B2 * | 1/2013 | Tyber | A61B 17/8605 606/301 |
| 8,460,343 | B2 | 6/2013 | Graham | |
| 8,784,427 | B2 * | 7/2014 | Fallin | A61B 17/1739 606/103 |
| 9,241,784 | B2 * | 1/2016 | Fallin | A61B 17/1739 |
| 9,289,220 | B2 * | 3/2016 | Wolfe | A61B 17/1775 |
| 9,687,250 | B2 * | 6/2017 | Dayton | A61B 17/1682 |
| 9,888,949 | B2 | 2/2018 | Johnson | |
| 9,949,744 | B2 | 4/2018 | McCormick | |
| 9,955,963 | B2 * | 5/2018 | Fallin | A61B 17/0483 |
| 10,022,170 | B2 * | 7/2018 | Leemrijse | A61B 17/86 |
| 10,206,692 | B2 * | 2/2019 | Sanders | A61B 17/17 |
| 10,226,292 | B2 * | 3/2019 | Lundquist | A61B 17/809 |
| 10,258,328 | B2 * | 4/2019 | Penzimer | A61B 17/8605 |
| 10,292,713 | B2 * | 5/2019 | Fallin | A61B 17/151 |
| 10,342,529 | B2 * | 7/2019 | Fallin | A61B 17/0469 |
| 10,342,590 | B2 * | 7/2019 | Bays | A61B 17/15 |
| 10,376,268 | B2 * | 8/2019 | Fallin | A61B 17/151 |
| 10,881,436 | B2 * | 1/2021 | Muller | A61B 17/1775 |
| 11,020,148 | B2 * | 6/2021 | Hollis | A61B 17/15 |
| 11,547,425 | B1 * | 1/2023 | Lebrija | A61B 17/66 |
| 2004/0111090 | A1 * | 6/2004 | Dahners | A61B 17/80 606/297 |
| 2005/0033302 | A1 * | 2/2005 | Frank | A61B 17/68 606/907 |
| 2006/0015102 | A1 * | 1/2006 | Toullec | A61B 17/8095 606/281 |
| 2007/0265634 | A1 * | 11/2007 | Weinstein | A61B 17/15 606/87 |
| 2009/0036931 | A1 * | 2/2009 | Pech | A61B 17/7291 606/62 |
| 2009/0222047 | A1 * | 9/2009 | Graham | A61B 17/8061 606/280 |
| 2011/0009912 | A1 * | 1/2011 | Gonzalez-Hernandez | A61B 17/7291 606/328 |
| 2011/0093084 | A1 * | 4/2011 | Morton | A61B 17/1682 606/86 R |
| 2011/0093085 | A1 * | 4/2011 | Morton | A61B 17/15 623/21.19 |
| 2011/0230884 | A1 * | 9/2011 | Mantzaris | A61B 17/8605 606/64 |
| 2012/0016428 | A1 * | 1/2012 | White | A61B 17/68 606/86 R |
| 2013/0123864 | A1 | 5/2013 | Gonzalez-Hernandez | |
| 2015/0327900 | A1 * | 11/2015 | Toro | A61B 17/8061 606/280 |
| 2016/0038186 | A1 * | 2/2016 | Herzog | A61B 17/686 606/328 |
| 2016/0199076 | A1 * | 7/2016 | Fallin | A61B 17/1739 606/301 |
| 2016/0235414 | A1 * | 8/2016 | Hatch | A61B 17/151 |
| 2017/0014143 | A1 * | 1/2017 | Dayton | A61B 17/8061 |
| 2017/0079669 | A1 * | 3/2017 | Bays | A61B 17/1739 |
| 2017/0172638 | A1 * | 6/2017 | Santrock | A61B 17/8061 |
| 2017/0196602 | A1 * | 7/2017 | Lundquist | A61B 17/7291 |
| 2018/0028242 | A1 * | 2/2018 | Parekh | A61B 17/7291 |
| 2018/0070995 | A1 * | 3/2018 | Kay | A61B 17/1717 |
| 2018/0110530 | A1 * | 4/2018 | Wagner | A61B 17/8061 |
| 2018/0161170 | A1 * | 6/2018 | Petranto | A61F 2/4225 |
| 2018/0214163 | A1 | 8/2018 | McCormick | |
| 2018/0242987 | A1 * | 8/2018 | Lintula | A61B 17/72 |
| 2018/0250024 | A1 * | 9/2018 | Woodard | A61B 17/1775 |
| 2018/0280069 | A1 * | 10/2018 | Barmes | A61B 17/1717 |
| 2018/0353301 | A1 * | 12/2018 | Goldstein | A61F 2/4225 |
| 2019/0117286 | A1 * | 4/2019 | Tyber | A61B 17/68 |
| 2019/0125418 | A1 | 5/2019 | Muller | |
| 2019/0175236 | A1 * | 6/2019 | Blacklidge | A61B 17/1775 |
| 2019/0274745 | A1 * | 9/2019 | Smith | A61B 17/8061 |
| 2022/0354513 | A1 * | 11/2022 | Bregman | A61B 17/151 |
| 2023/0043795 | A1 * | 2/2023 | Hollis | A61B 17/1697 |

* cited by examiner

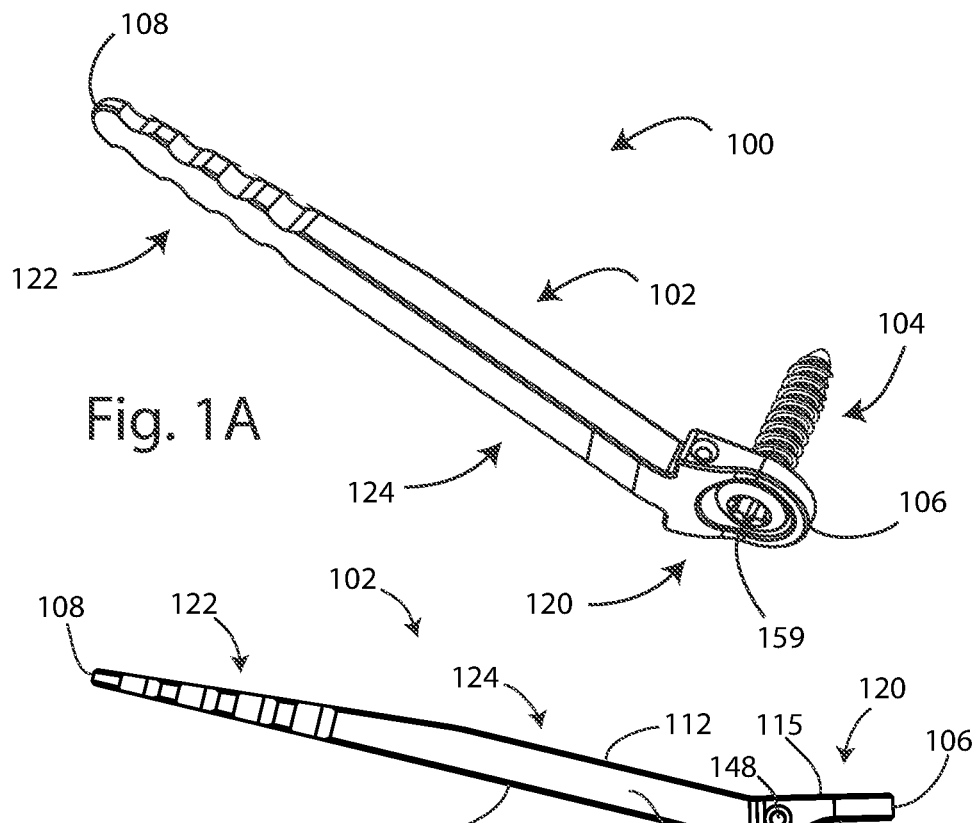
Fig. 1A
Fig. 1B
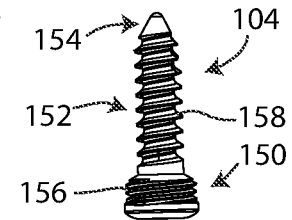
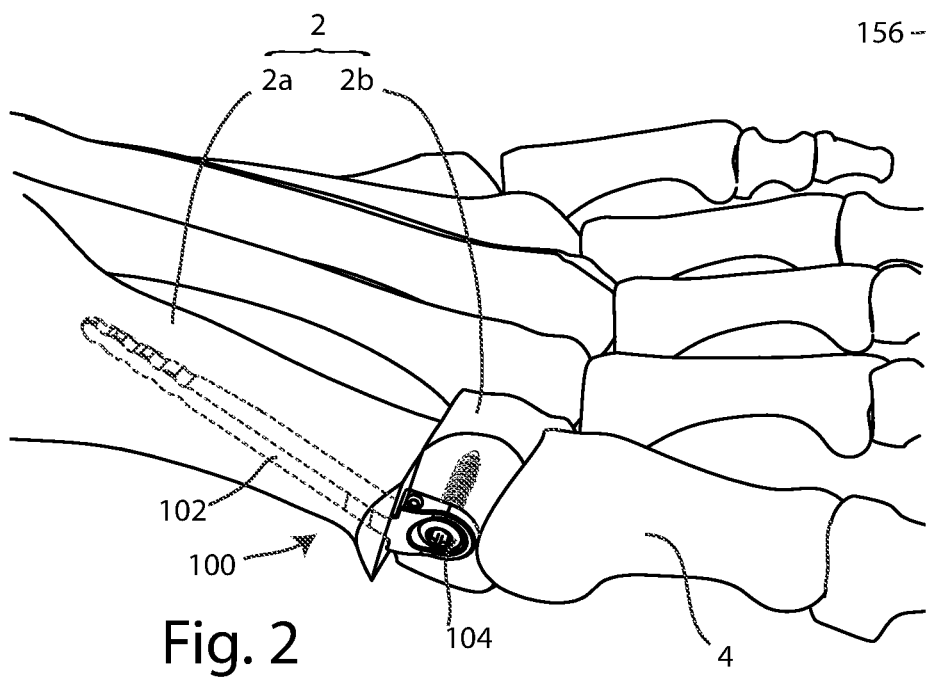
Fig. 2

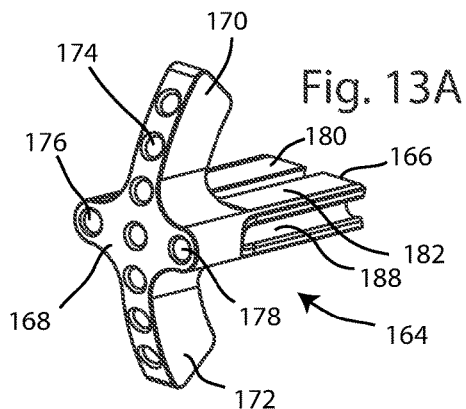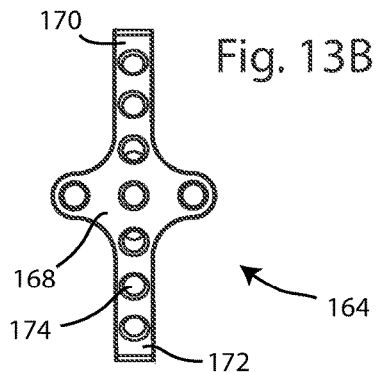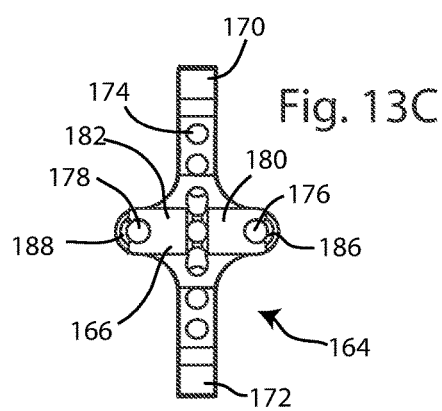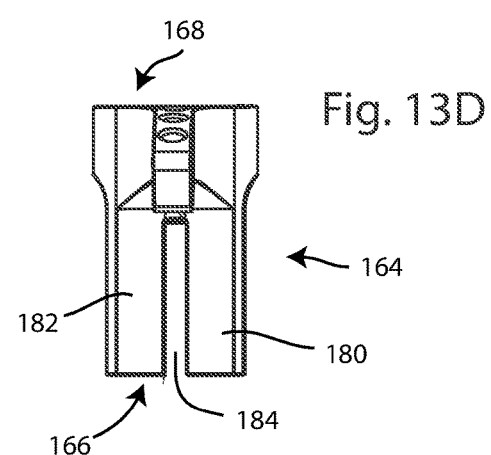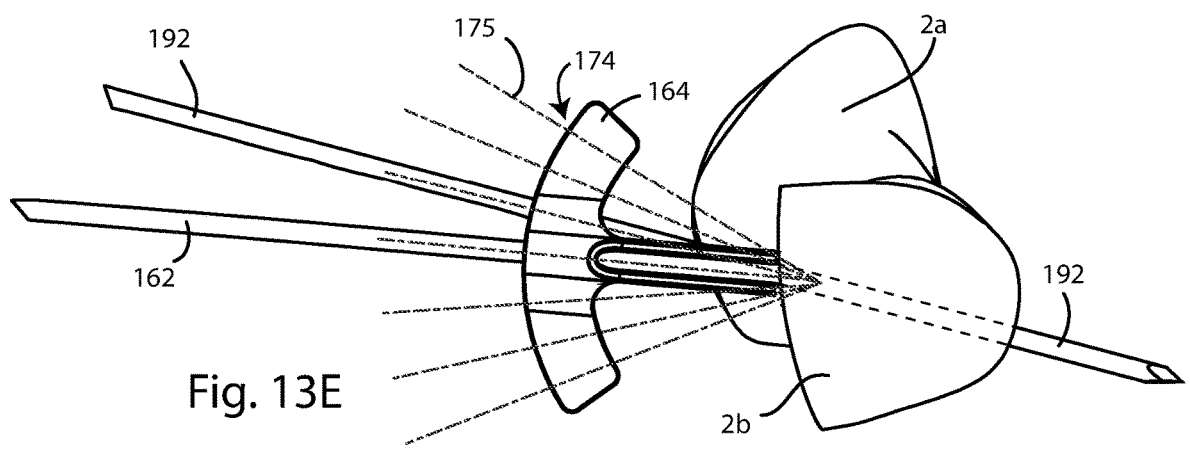

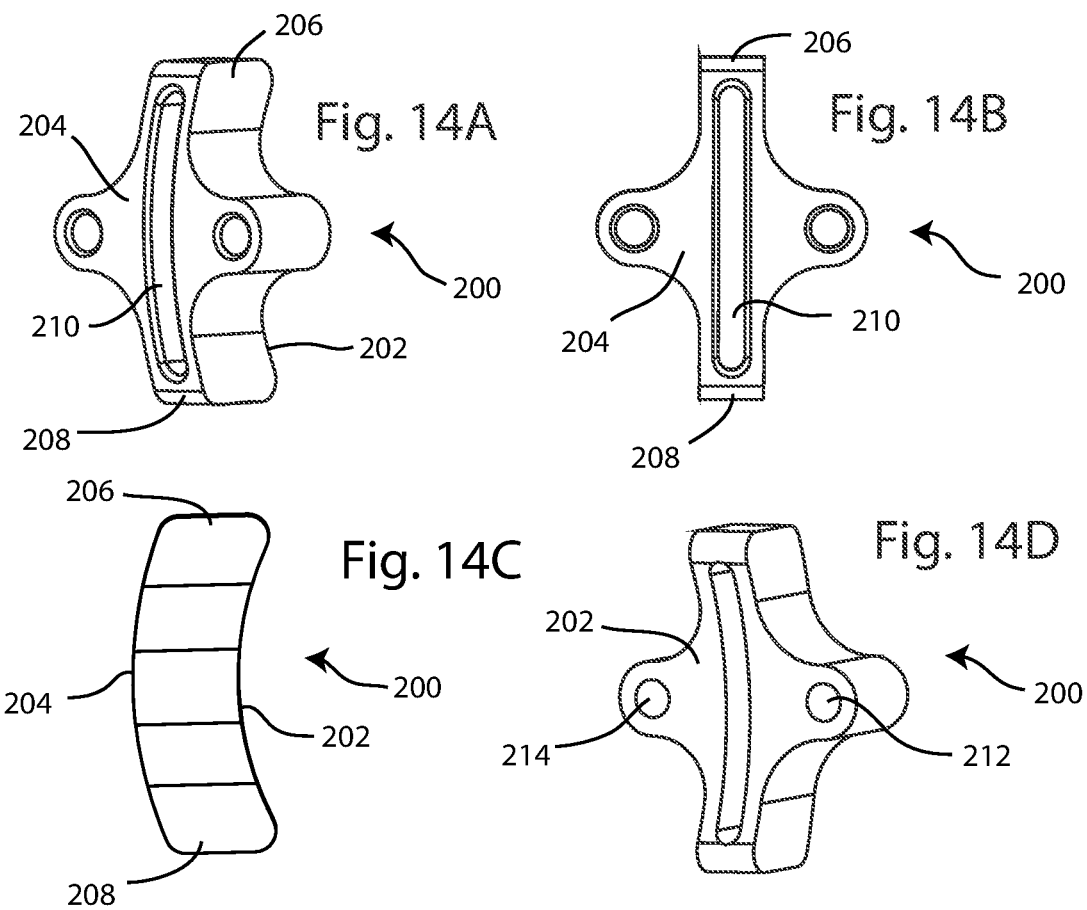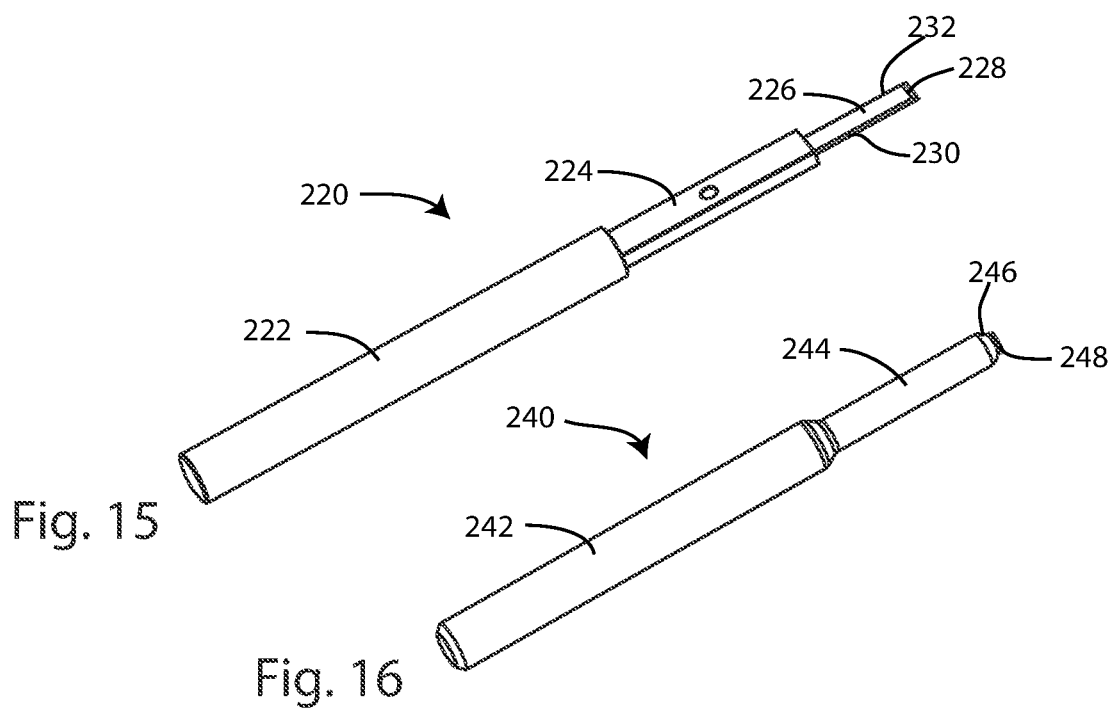

BUNION CORRECTION SYSTEM AND METHOD

CROSS-REFERENCE TO RELATED APPLICATIONS

The present application is a continuation of:
U.S. patent application Ser. No. 16/033,086, entitled BUNION CORRECTION SYSTEM AND METHOD, filed Jul. 11, 2018.

The foregoing is incorporated by reference as though set forth herein in its entirety.

TECHNICAL FIELD

The present invention relates to surgical treatment for deformities of the foot. More specifically, the present invention relates to implants, instrumentation and methods for minimally invasive bunion correction.

BACKGROUND

Bunions are a progressive disorder typically beginning with a leaning of the great toe, which may gradually change the angle of the bones and produce a characteristic bump on the medial side of the metatarsal near the joint of the metatarsal with the proximal phalanx. Specifically, the bunion is the prominence made of bone and at times an inflamed bursa. Hallux valgus is the condition in which the great toe deviates from the normal position toward the direction of the second toe.

Bunion correction or repair is a common surgery with over 100,000 surgeries performed annually in the US. Many surgical procedures for bunion repair are invasive and painful, requiring an incision of several inches and a long period of convalescence, of up to 10-12 weeks. Minimally invasive surgery has been performed in orthopedics for decades. However, creating the bone cuts has been performed with burrs and drill bits inserted blindly through small incisions. This method of surgery lends itself to potential adjacent soft tissue damage and unrepeatable results from patient to patient. The disclosure contained herein seeks to remedy this problem by providing an instrumented technique and guides to provide repeatability and limit the damage to tissue along with a simple implant insertion technique.

Disclosed herein is an implant and method for bunion repair which can be performed as a minimally invasive procedure, thus reducing discomfort, scarring and recovery time in comparison with more invasive bunion correction procedures.

SUMMARY OF THE INVENTION

The various systems and methods of the present invention have been developed in response to the present state of the art, and in particular, in response to the problems and needs in the art that have not yet been fully solved by currently available techniques. The systems and methods of the present invention may provide techniques for bunion correction which result in a streamlined procedure, faster recovery, reduced scarring, and reduced discomfort during healing.

To achieve the foregoing, and in accordance with the invention as embodied and broadly described herein, in a first aspect of the disclosure, a method for correcting a bunion formed at a joint between a metatarsal and a great toe includes selecting a target location on the metatarsal; creating an osteotomy in the metatarsal at the target location, the osteotomy resecting the metatarsal into a first metatarsal portion and a separate second metatarsal portion; implanting an implant into the metatarsal, the implant including a monolithic body having a head and an anchor, wherein implanting the implant into the metatarsal includes inserting the anchor into the intramedullary canal of the first metatarsal portion; securing a length of suture to the great toe; tensioning the suture to re-align the great toe relative to the first metatarsal portion; and attaching the length of suture to the implant head.

Various embodiments of the first aspect can include one or more of the following steps or attributes. Inserting at least one k-wire into the metatarsal adjacent to the target location. Mounting a guide block onto the k-wire, wherein the guide block defines a cutting slot. Actuating a cutting tool through the cutting slot to create the osteotomy in the metatarsal. The cutting tool is selected from the group consisting of a broach, a saw, a blade, a chisel, an osteotome, a curette, a pick, and a rasp. Attaching the implant head to the second metatarsal portion. The incision is 0.5 inch or less in length.

In a second aspect of the disclosure, a method for correcting a bunion formed at a joint between a metatarsal and a great toe includes: selecting a target location on the metatarsal; positioning a guide block at the target location; guiding a cutting instrument with the guide block to create an osteotomy in the metatarsal at the target location, the osteotomy dividing the metatarsal into a first metatarsal portion and a separate second metatarsal portion; implanting an implant into the metatarsal, the implant including a monolithic body having a head and an anchor, wherein implanting the implant into the metatarsal includes inserting the anchor into the intramedullary canal of the first metatarsal portion; securing a length of suture to the great toe; tensioning the suture to re-align the great toe relative to the first metatarsal portion; and attaching the length of suture to the implant head.

Various embodiments of the second aspect can include one or more of the following steps or attributes. Inserting at least one k-wire into the metatarsal adjacent to the target location; mounting the guide block onto the k-wire, wherein the guide block defines a cutting slot; and actuating the cutting instrument through the cutting slot to create the osteotomy in the metatarsal. The cutting instrument is selected from the group consisting of a broach, a saw, a blade, a chisel, an osteotome, a curette, a pick, and a rasp. A joint capsule surrounds the joint, wherein securing the length of suture to the great toe includes securing the length of suture to the joint capsule. Attaching the implant head to the second metatarsal portion. The incision is 0.5 inch or less in length.

In a third aspect of the disclosure, a method for correcting a bunion formed at a joint between a metatarsal and a great toe includes: selecting a target location on the metatarsal; creating an osteotomy in the metatarsal at the target location, the osteotomy dividing the metatarsal into a first metatarsal portion and a separate second metatarsal portion; implanting an implant into the metatarsal, the implant including a monolithic body having a head and an anchor, wherein implanting the implant into the metatarsal includes implanting the anchor into the first metatarsal portion; securing a length of suture to a joint capsule surrounding the joint; tensioning the length of suture to re-align the great toe relative to the first metatarsal portion; attaching the length of suture to the implant head; and fastening the implant head to the second metatarsal portion.

Various embodiments of the third aspect can include one or more of the following steps or attributes. The first metatarsal portion is proximal to the second metatarsal portion. Translating the second metatarsal portion to expose a distal-facing surface of the first metatarsal portion; and inserting the implant anchor through the distal-facing surface into the intramedullary canal of the first metatarsal portion. Abutting the implant head against the distal-facing surface on the first metatarsal portion. The implant head further includes a transverse bore, wherein attaching the length of suture to the implant head includes passing the suture through the transverse bore. Making an incision along a side of the metatarsal before selecting the target location, creating the osteotomy, implanting the implant, securing the length of suture to the joint capsule, tensioning the length of suture, attaching the length of suture to the implant head, and fastening the implant head to the second metatarsal portion; and closing the incision after selecting the target location, creating the osteotomy, implanting the implant, securing the length of suture to the joint capsule, tensioning the length of suture, attaching the length of suture to the implant head, and fastening the implant head to the second metatarsal portion, wherein the suture is a non-resorbable suture, and wherein the length of suture remains secured to the joint capsule and attached to the implant after closing the incision.

These and other features and advantages of the present invention will become more fully apparent from the following description and appended claims, or may be learned by the practice of the invention as set forth hereinafter.

BRIEF DESCRIPTION OF THE DRAWINGS

Exemplary embodiments of the invention will become more fully apparent from the following description and appended claims, taken in conjunction with the accompanying drawings. Understanding that these drawings depict only exemplary embodiments and are, therefore, not to be considered limiting of the invention's scope, the exemplary embodiments of the invention will be described with additional specificity and detail through use of the accompanying drawings in which:

FIG. 1A is a perspective view of a bunion correction implant, comprising a nail and a fastener, according to one embodiment of the invention; FIG. 1B is an exploded view of the implant;

FIG. 2 is a perspective view of a partial skeleton of a foot, with the implant of FIG. 1A implanted into the first metatarsal;

FIG. 13A is a perspective view of the first guide of FIG. 5; FIG. 13B is a medial view of the first guide of FIG. 5; FIG. 13C is a lateral view of the first guide of FIG. 5; FIG. 13D is a superior view of the first guide of FIG. 5; FIG. 13E is a distal view of the distal end of the metatarsal, the first guide, and the trocar of FIG. 6 extending through another one of the guide holes, with dotted lines indicating the trajectories of the plurality of guide holes;

FIG. 14A is a medial perspective view of the second guide of FIG. 7; FIG. 14B is a medial view of the second guide of FIG. 7; FIG. 14C is a side view of the second guide of FIG. 7; FIG. 14D is a lateral perspective view of the second guide of FIG. 7;

FIG. 15 is a perspective view of the broach of FIG. 8; and

FIG. 16 is a perspective view of the implant inserter of FIG. 10.

DETAILED DESCRIPTION

Figure 3A:
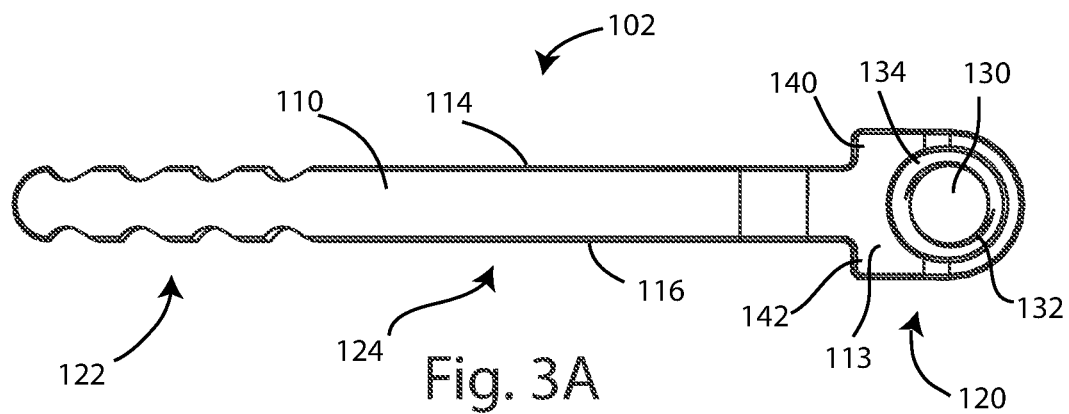
FIG. 3A is medial view of the nail of FIG. 1A.

Exemplary embodiments of the invention will be best understood by reference to the drawings, wherein like parts are designated by like numerals throughout. It will be readily understood that the components of the invention, as generally described and illustrated in the Figures herein, could be arranged and designed in a wide variety of different configurations. Thus, the following more detailed description of the embodiments of the apparatus, system, and method, as represented in FIGS. 1A through 16, is not intended to limit the scope of the invention, as claimed, but is merely representative exemplary of exemplary embodiments of the invention.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

Directional and/or relational terms such as, but not limited to, left, right, superior, inferior, top, bottom, vertical, horizontal, medial, and lateral are relative to each other, are dependent on the specific orientation of an applicable element or article, are used accordingly to aid in the description of the various embodiments in this specification and the appended claims, and are not necessarily intended to be construed as limiting. Standard medical terminology may be used to describe human anatomy, or the relationship of objects to the human anatomy. For example, proximal refers to an object or anatomical element closer to the center of the body, while distal refers to an object or anatomical element farther away from the center of the body.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Referring to FIG. 1A, a bunion correction implant system 100 according to one embodiment of the invention includes a nail 102 and a fastener 104. As seen in FIG. 2, the nail 102 may be implanted to extend longitudinally into a proximal portion 2a of a resected metatarsal 2, and the fastener 104 inserted through a portion of the nail to secure it to the distal portion 2b of the metatarsal 2. The bunion correction implant system 100 may further include a suture which may be routed through the medial capsule of the metatarsophalangeal (MTP) joint, secured in the soft tissues of the great toe, tensioned to re-align the position of the proximal phalanx 4 relative to the metatarsal, and secured to the nail.

Referring to FIGS. 1A-B, and 3A-C, the implant nail 102 is a monolithic body extending from a first end 106 which may be a distal end, to a second end 108 which may be a proximal end. The nail 102 may be generally rectangular in cross-section, having a medial side 110 which may be an outer side, a lateral side 112 which may be an inner side, a superior side 114, and an inferior side 116. The nail 102 includes a head 120, an anchor 122, and a neck 124 extending between the head 120 and the anchor 122.

Figure 3B:
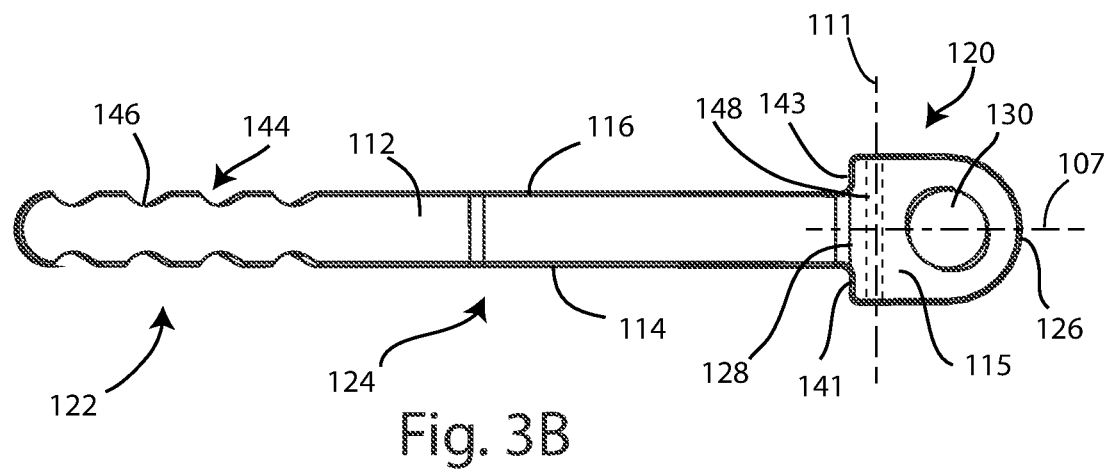
FIG. 3B is lateral view of the nail of FIG. 1A.
Figure 3C:
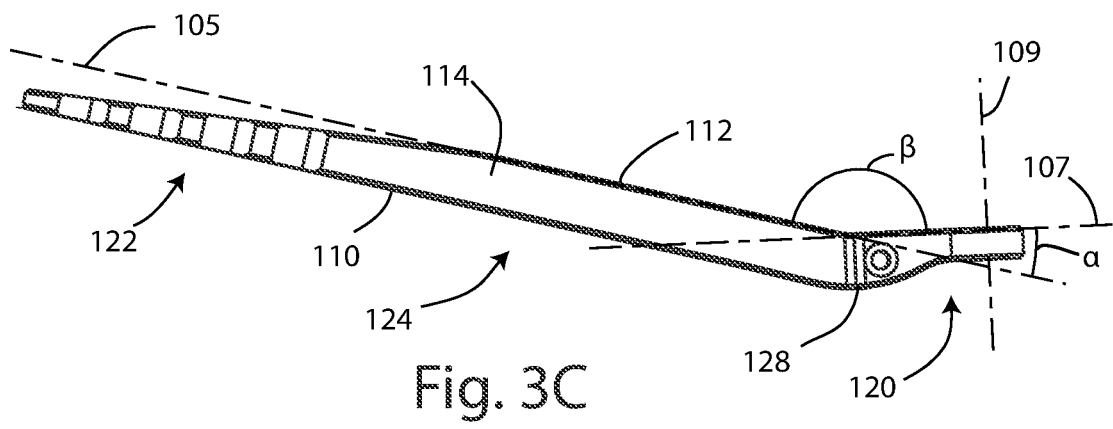
FIG. 3C is a superior view of the nail of FIG. 1A.

With particular reference to FIGS. 3B and 3C, the nail anchor 122 and neck 124 extend along a longitudinal axis 105, and the nail head 120 extends distally away from the neck 124 at an angle. The nail head extends between a head first end 126 and a head second end 128 along a head first axis 107. In the embodiment depicted, the angle α between the head first axis 107 and the longitudinal axis 105 is 15°, with an angle β between the neck lateral surface and the head lateral surface of 165°. In other embodiments of the invention, angle α may be in the range of 0° to 25°. In at least the embodiment depicted, the nail 102 and assembled implant 100 are bilaterally symmetrical with respect to the longitudinal axis 105, and with respect to the head first axis 107.

The nail head 120 includes an opening 130 centered on a head second axis 109, which is perpendicular to the head first axis 107. The head second axis may extend generally medially-laterally (ML) upon implantation. In the embodiment depicted, the opening 130 extends between a head lateral side 115 and a head medial side 113, and includes threads 132 for engagement with the fastener 104, although additional embodiments may lack threads. A concave lip 134 encircles the opening 130. The head second end 128 is wider than the neck 124 with respect to the superior-inferior dimension, and includes a first shoulder 140 and a second shoulder 142, the shoulders 140, 142 projecting superiorly and inferiorly, respectively, away from the neck 124 at the intersection of the neck and the head. The first shoulder 140 includes a first proximal shoulder surface 141, and the second shoulder 142 includes a second proximal shoulder surface 143. The proximal shoulder surfaces 141, 143 face proximally away from the head 120 and are at right angles to the neck superior and inferior sides 114, 116. The head 120 may further include a transverse bore 148, extending along a head third axis 111 which is perpendicular to the head first axis 107 and the head second axis 109. The head third axis 111 may extend generally superiorly-inferiorly (SI) upon implantation. In the embodiment depicted, the thickness of the head 120 between its medial 113 and lateral 115 sides increases between the head first end 126 and the head second end 128, so that the thickest part of the head is at the shoulders 140, 142.

The neck 124 extends between and connects the head 120 with the anchor 122. The thickness of the neck 124 between the medial 110 and lateral 112 sides can vary depending on the desired degree of shift of the metatarsal. In at least the embodiment depicted, the neck thickness tapers between the head 120 and the anchor 122. The width of the neck 124 between the superior 114 and inferior 116 sides may also vary. The length of the nail between the first and second ends 106, 108 can vary, as can the relative lengths of the head, neck, and/or anchor portions. The anchor 122 is coaxial with the neck 124, and extends from the neck to the second end 108 of the nail. Both the thickness of the anchor between the medial 110 and lateral 112 sides, and the width of the anchor between the superior 114 and inferior 116 sides may taper towards the nail second end, promoting easy insertion of the nail into bone. The anchor terminal end may be rounded as in the embodiment depicted in FIGS. 2A and 2B; in other embodiments it may be pointed, flattened, serrated, or another shape. The anchor 122 includes a plurality of bone engagement features 144 which may be shaped as teeth, scallops, serrations, or other shapes to promote engagement within bone. For example, the scallops 146 in the embodiment depicted provide surface irregularities which resist nail backup. In the embodiment shown, the neck and anchor are free from openings; other embodiments could include openings for supplementary fixation or instrument connection.

Fastener 104 includes a fastener head 150, fastener shaft 152, and tip 154. The head 150 includes threads 156 for locking engagement with threads 132 in the nail head 120; other embodiments may lack threads 156. The shaft 152 includes threads 158 for engagement in bone. The head 150 may include a driving feature 159 for engagement with a driver. In the embodiment depicted, fastener 104 is a locking screw type fastener; in other embodiments the fastener may be locking or non-locking, and may be polyaxially adjustable or non-polyaxially adjustable.

The nail 102 and fastener 104 may comprise titanium, stainless steel, polyether ether ketone (PEEK), nitinol, and/or other rigid biocompatible materials or combinations thereof. The suture is a non-resorbable suture, although other embodiments may include a resorbable suture.

Referring to FIGS. 4-16, a method of correcting a bunion includes one or more of the following steps. Although the steps are described in an order, in other embodiments of the method one or more of the steps may be repeated, omitted, or performed in a different order.

Figure 4:
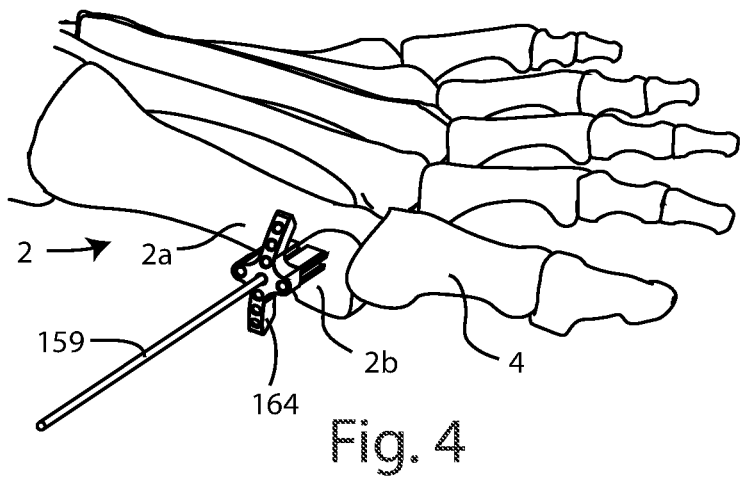
FIG. 4 is a perspective view of the foot skeleton with a k-wire inserted into the metatarsal and a first guide mounted on the k-wire, the first guide having a plurality of guide holes.
Figure 5:
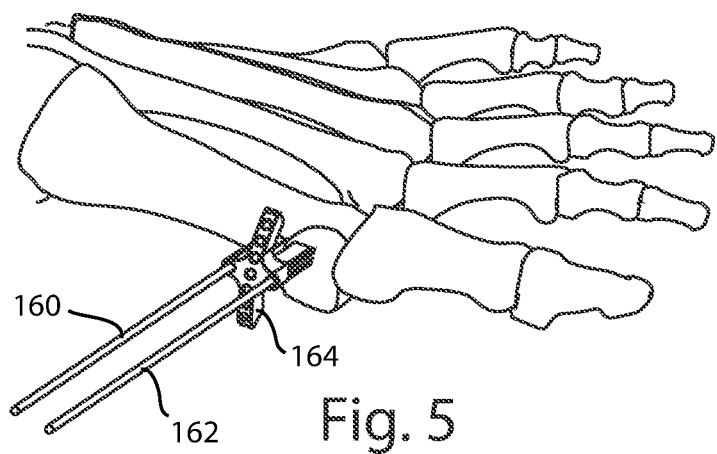
FIG. 5 is a perspective view of the foot skeleton, k-wire and guide of FIG. 4, with additional k-wires inserted into the metatarsal.

A small incision is made in the affected metatarsal at the medial side of the bunion. Preferably, the incision is 0.5 inch long or less. Referring to FIG. 4, a first k-wire 159 is introduced through the incision and into the metatarsal at a selected target location. A first guide block 164 is mounted onto the k-wire 159 and urged toward the metatarsal 2. Referring to FIG. 5, second and third k-wires 160, 162 are introduced through the guide block 164 into the metatarsal, on either side of the selected target location. The second k-wire 160 is located in a first metatarsal portion 2a, and the third k-wire 162 is introduced into a second metatarsal portion 2b. The first k-wire 159 is removed from the metatarsal.

As shown in FIGS. 13A-E, the first guide block 164 extends between a first or lateral side 166, and a second or medial side 168. First and second guide portions 170, 172 project superiorly and inferiorly, respectively. A series of guide holes 174 extend through the guide block, each defining a trajectory 175, which converge at a common point, as seen in FIG. 13E. The guide holes 174 and their trajectories 175 are coplanar, defining a cutting plane when the first guide block 164 is mounted on the k-wires 160, 162. A pair of mounting holes 176, 178 are sized to slide over the k-wires. First and second mounting supports 180, 182 extend medially from the guide block 164 and are separated by a gap 184. The mounting supports 180, 182 include slots 186, 188 for guiding and supporting the k-wires, and prevent rotation of the guide block 164 once mounted. The medial side 168 of the guide block 164 may be convexly curved as shown.

Figure 6:
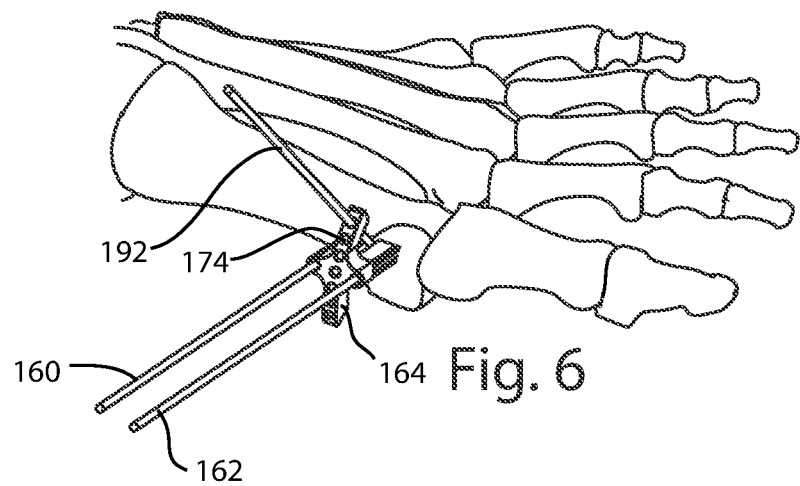
FIG. 6 is a perspective view of the foot skeleton, k-wires and first guide of FIG. 5, with a trocar extending through one of the guide holes to create a hole in the metatarsal.

Referring to FIGS. 6 and 13E, after the first guide block 164 is mounted on the k-wires and abuts the metatarsal 2, a trocar 192, reamer or other instrument is introduced through one of the guide holes 174 and inserted into the metatarsal 2 to create a hole through the metatarsal along the trajectory of the guide hole. The trocar 192 may then be inserted through more of the guide holes 174 and through the metatarsal. This step creates a linear series of openings through the bone at the targeted location, weakening the bone at that location in preparation for a subsequent osteotomy to resect the metatarsal head. After the desired number of openings are created, the first guide block 164 is withdrawn from the k-wires.

Figure 7:
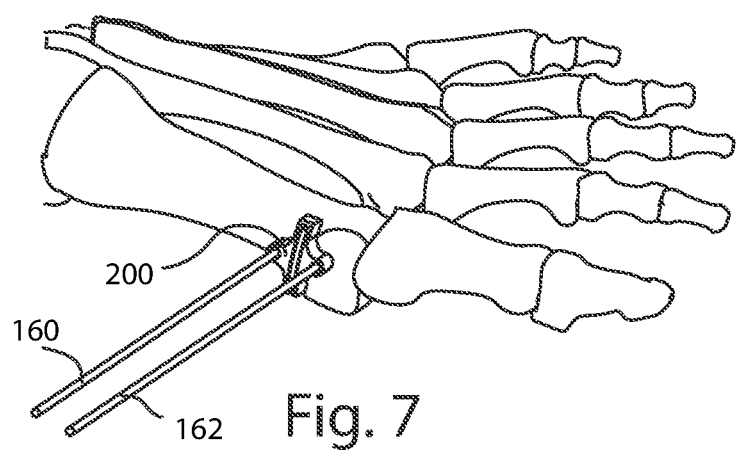
FIG. 7 is a perspective view of the foot skeleton and k-wires of FIG. 5, with a second guide mounted on the k-wires.

Referring to FIG. 7, a second guide block 200 is introduced onto the k-wires 160, 162. As shown in FIGS. 14A-D, the second guide block 200 extends between a first or lateral side 202, and a second or medial side 204. First and second guide portions 206, 208 project superiorly and inferiorly, respectively. A cutting slot 210 extends through the guide block 200, opening out on the lateral and medial sides 202, 204, and mounting holes 212, 214 extend between the medial and lateral sides for mounting the block on the k-wires. The guide block 200 may be curved as shown, wherein the medial side 204 of the guide block 200 is convexly curved and the lateral side 202 is concave. At least the concave lateral surface may allow the guide to fit closely against the targeted location. When the second guide block 200 is mounted on the k-wires 160, 162, the mid-plane of the opening defined by the cutting slot 210 is coplanar or at least parallel with the cutting plane defined by the first guide block guide holes 174 and trajectories 175, and with the series of openings created in the bone in the previous step.

Figure 8:
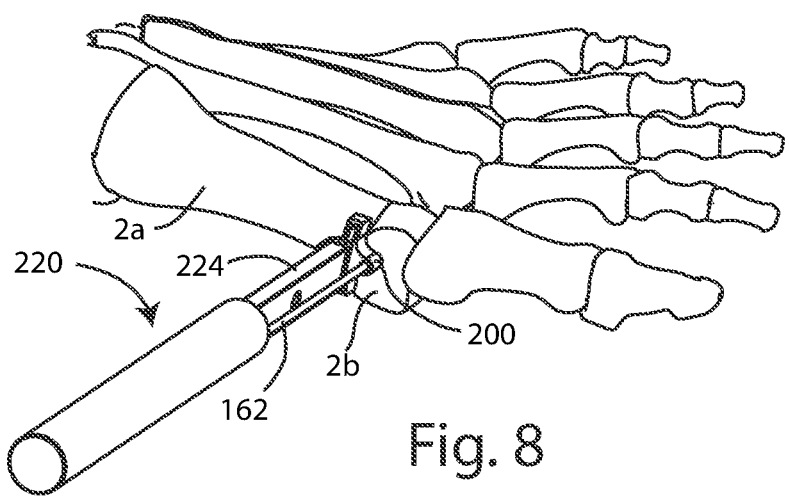
FIG. 8 is a perspective view of the foot skeleton, k-wires and second guide of FIG. 7, with a broach extending through a guide slot to cut an osteotomy in the metatarsal and separate the metatarsal into a proximal metatarsal portion and a distal metatarsal portion.

Referring to FIGS. 8 and 15, a broach 220 is used to create an osteotomy in the metatarsal 2, resecting the metatarsal into the first or proximal metatarsal portion 2a and the second or distal metatarsal portion 2b. The broach 220 includes a handle portion 222, a shaft portion 224, and a cutting portion 226 with a cutting tip 228 and cutting edges 230, 232. The cutting edges and tip may be beveled, sharpened, serrated and/or otherwise configured to cut through bone. The broach cutting portion 226 is urged laterally through the cutting slot 210 and into the bone to create the osteotomy. The shaft portion 224 may act as a stop to limit lateral insertion of the cutting portion through the cutting slot. In other embodiments of the method, instead of or in combination with broach 220, a saw, blade, chisel, osteotome, curette, pick, rasp or other instrument or combinations thereof may be used to perform the osteotomy. When the osteotomy step is completed, the second guide block 200 is removed from the k-wires.

Figure 9:
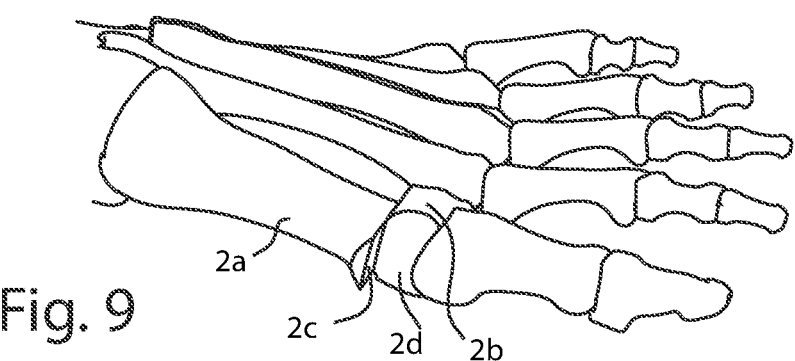
FIG. 9 is a perspective view of the foot skeleton of FIG. 8, with the distal metatarsal portion shifted laterally relative to the proximal metatarsal portion.

Referring to FIG. 9, the now separate distal metatarsal bone portion 2b is translated laterally relative to proximal metatarsal bone portion 2a. A generally flat distal-facing surface 2c on the proximal metatarsal portion 2a is exposed, and it is into this surface that the nail 102 is implanted. Distal-facing surface 2c of the proximal metatarsal bone portion 2a, and a medial-facing surface 2d of the distal metatarsal bone portion 2b may be referred to as abutment surfaces. The degree of offset of the distal metatarsal portion may vary but is sufficient to permit implantation of nail 102 into the distal-facing surface 2c so that the nail head 120 does not protrude medially beyond the medial outer surface of the proximal metatarsal portion 2a after implantation. The k-wires 160, 162 may be removed before or after the shifting of the distal metatarsal portion relative to proximal metatarsal portion.

Figure 10:
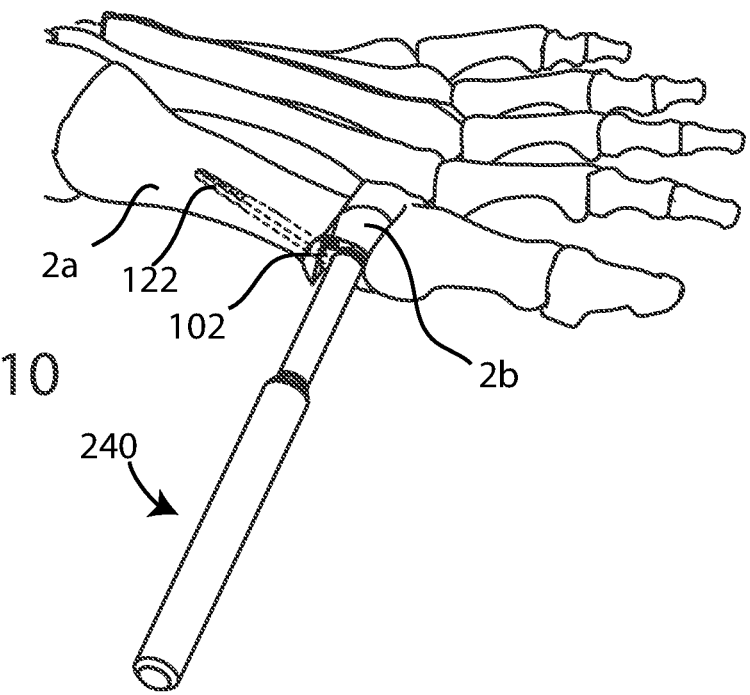
FIG. 10 is a perspective view of the foot skeleton of FIG. 9, with the nail of FIG. 1 mounted on an implant inserter and implanted into the proximal metatarsal portion.

Referring to FIGS. 10 and 16, the nail 102 is inserted through the incision and anchored into the prepared proximal metatarsal portion 2a. Prior to implantation, a suture 250 may be introduced to extend through the transverse bore 148. An implant inserter such as inserter 240 may be employed to implant the nail 102 into the bone. Inserter 240 comprises a handle portion 242, a shaft portion 244, and an implant engagement end 246. Threads 248 are formed on the implant engagement end 246, which may cooperate with the nail threads 132 to removably attach the nail 102 to the inserter 240. The inserter 240 is moved to insert the anchor 122 and neck 124 proximally into the distal-facing surface 2c and into the intramedullary canal of the metatarsal, leaving the head 120 distal to the proximal metatarsal portion 2a. If needed, the inserter 240 may be tapped to drive the nail 102 into position in the proximal metatarsal portion 2a. The nail 102 is positioned so that the proximal surfaces 141, 143 of shoulders 140, 142 abut the prepared distal-facing surface 2c of the metatarsal, and the nail head lateral side 115 is immediately adjacent to abutment surface 2d of the distal metatarsal portion 2b. When the nail 102 is properly seated in the desired location, the inserter 240 may be rotated to disengage it from the implanted nail 102.

Figure 12:
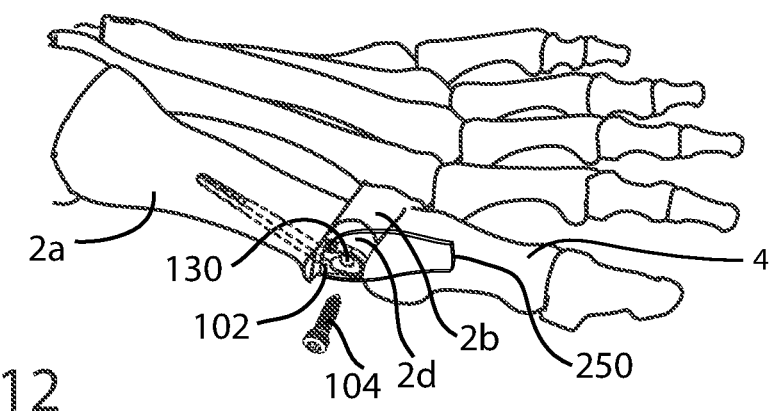
FIG. 12 is a perspective view of the foot skeleton of FIG. 10 showing the suture and the fastener aimed toward an opening of the nail.
Figure 11A:
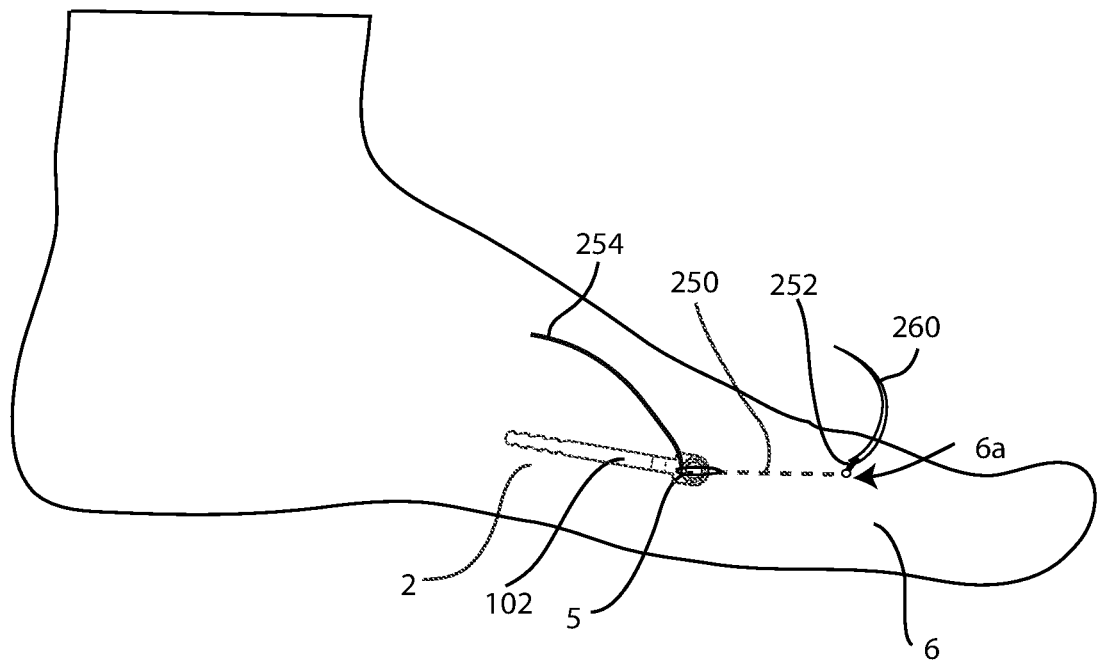
FIG. 11A is a medial view of the foot with the nail of FIG. 1 implanted in the proximal metatarsal portion and a needle and suture inserted into the foot through an incision at the site of the implant and exiting at a first location on the great toe at the proximal phalanx.
Figure 11B:
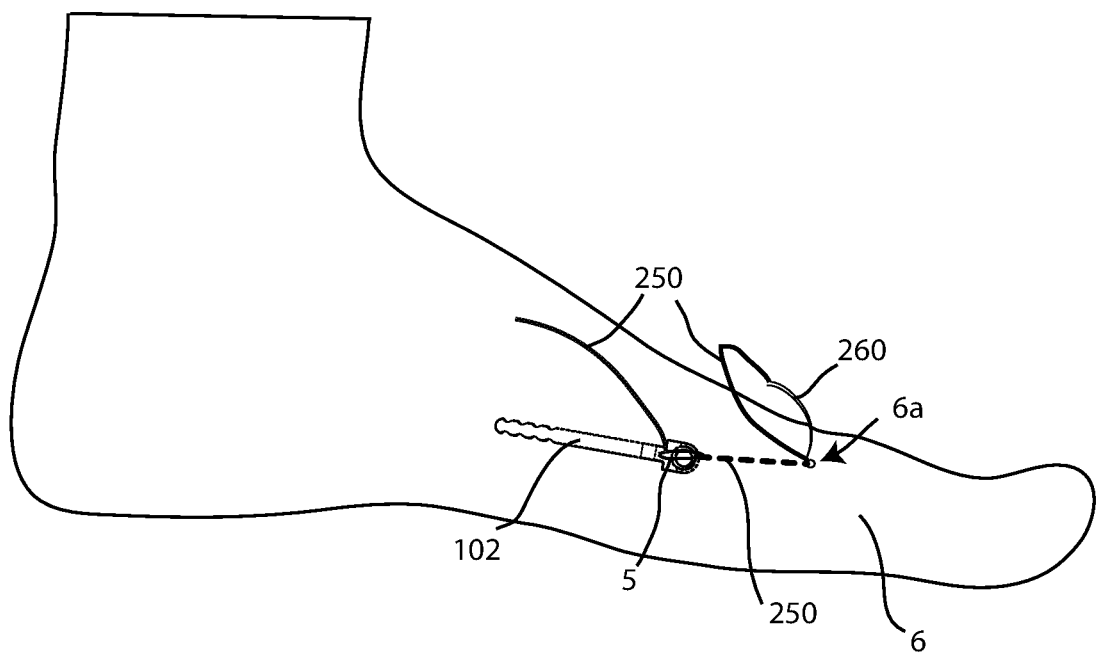
FIG. 11B is a medial view of the foot of FIG. 11A, with a first stitch being made at the first location on the great toe.
Figure 11C:
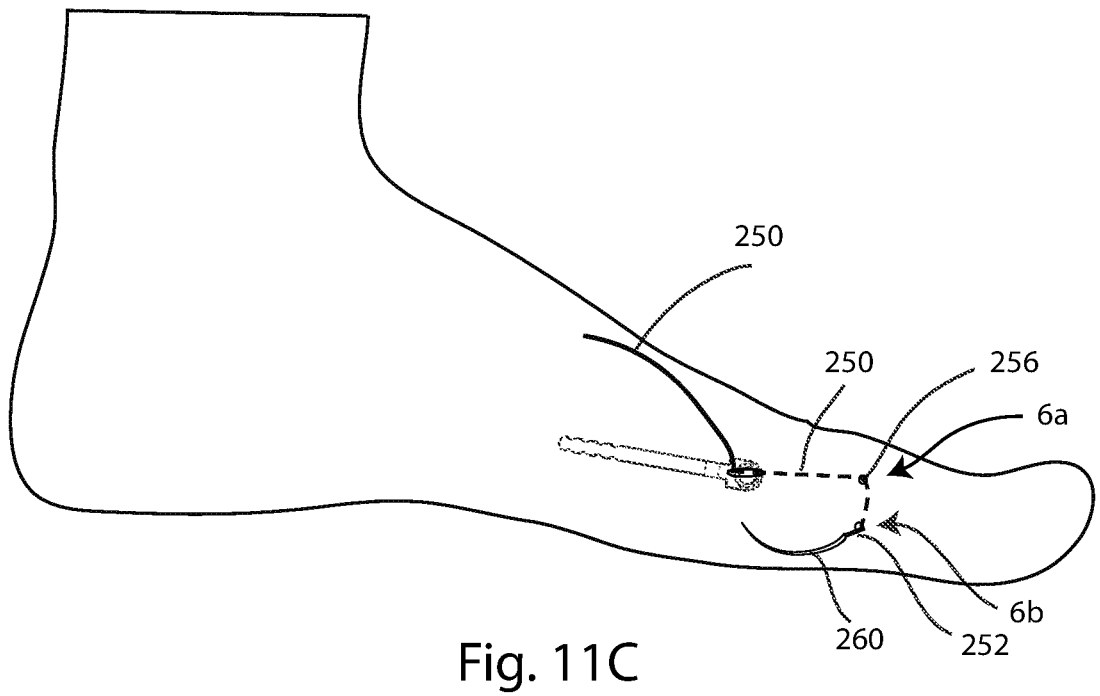
FIG. 11C is a medial view of the foot of FIG. 11B, with the needle emerging at a second location on the great toe.
Figure 11D:
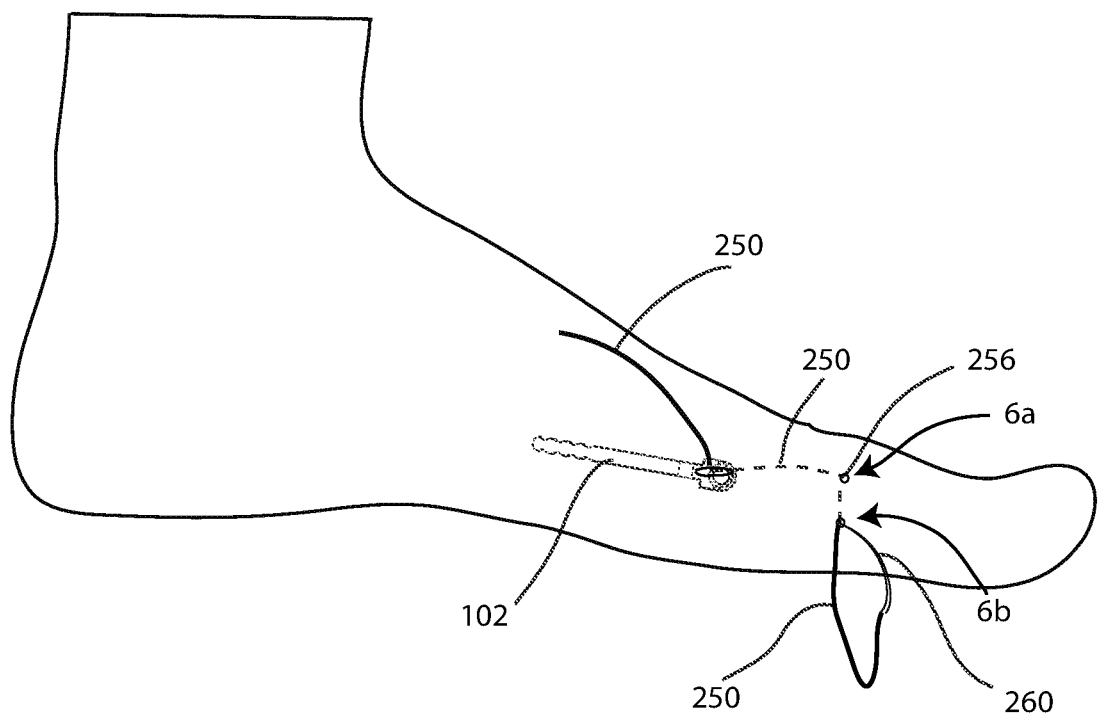
FIG. 11D is a medial view of the foot of FIG. 11C, with a second stitch being made at the second location on the great toe.
Figure 11E:
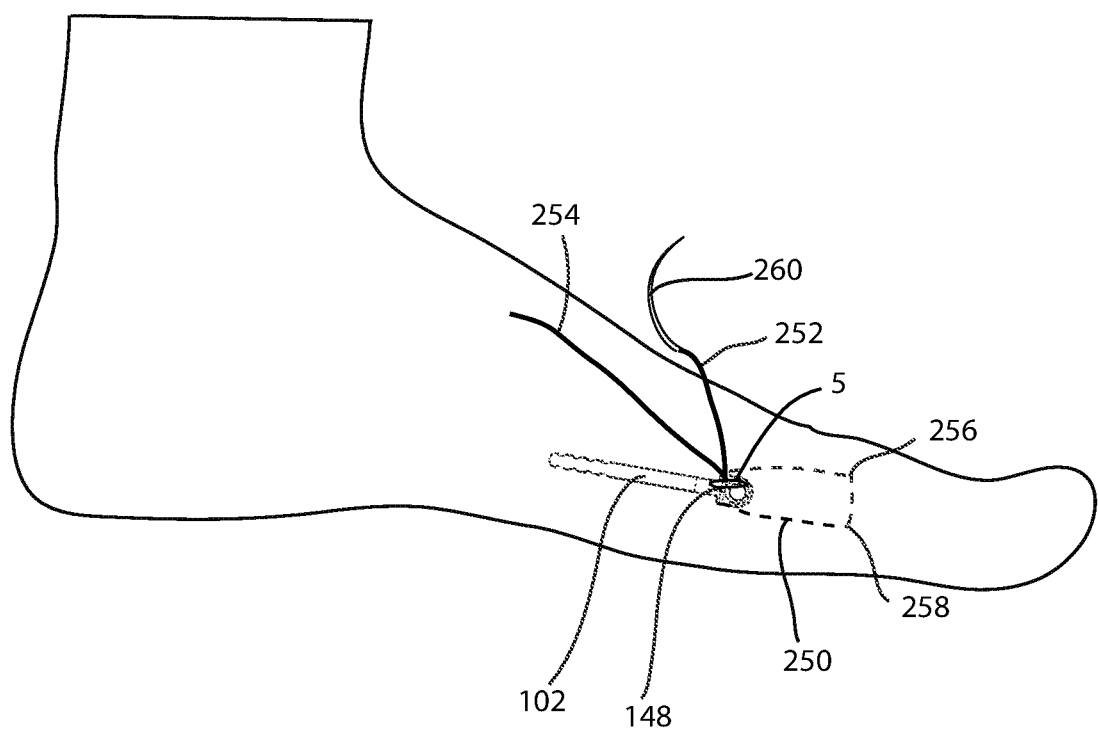
FIG. 11E is a medial view of the foot of FIG. 11D, with the suture routed through an implant bore, and the needle and suture emerging through the incision, and showing a path of the suture.

Referring to FIGS. 11A-11F and 12, the suture 250 may be engaged with implant 100 and secured to soft tissues of the great toe 6 to change the alignment of the phalanx 4 relative to the metatarsal 2 and correcting hallux valgus. As shown in FIG. 11A, a needle 260 carrying suture 250 is introduced through the incision 5, enters the medial capsule and emerges at a first location 6a on the epidermis of the great toe. The suture includes a first end 252 and a second end 254. As shown in FIG. 11B, the needle re-enters the skin at location 6a, creating a first stitch 256 in the soft tissue surrounding the phalanx 4. Continuing to FIG. 11C, the needle 260 and suture 250 emerge at a second location 6b on the epidermis of the great toe. Referring to FIG. 11D, the needle 260 and suture 250 re-enter the great toe at location 6b, creating a second stitch 258 in the soft tissue of the great toe 6. As shown in FIG. 11E, the needle and suture second end 252 emerge through the incision 5. The suture 250 is tensioned to change the alignment of the phalanx 4 relative to the metatarsal 2, providing tensile force along the medial side of the phalanx and correcting the hallux valgus. The nail shoulders 140, 142, abutting against the proximal metatarsal portion 2a act as a buttress to support the tension and alignment correction. The tensioned suture 250 is attached to the nail 102, with one or both of the first and second ends 252, 254 passing through the transverse bore 148. The suture first end 252 may pass through the transverse bore 148 from the inferior side 116 to the superior side 114 of the nail 102, and a knot 262 may be tied at the superior side of the bore 148, maintaining the suture tension and the correction. The knot 262 may be wider than the diameter of the transverse bore 148, so that the knot cannot pass through the bore. After knotting, the remaining suture free ends 252, 254 may be trimmed off. As seen in FIGS. 11E and 12, the suture 250 may follow a three-sided path from the implant 100 to the first and second stitches in the great toe, and back to the implant 100.

Referring to FIGS. 12 and 2, the screw tip 154 and shaft 152 are inserted through the nail opening 130 to secure the nail head 120 to the distal metatarsal portion 2b. As the shaft threads 158 engage in the bone, the nail head 120 lateral side 115 is urged to abut surface 2d of the distal metatarsal portion 2b. The screw head threads 156 engage with the nail opening threads 132 to lock the screw 104 to the nail 102. The incision 5 is closed. Following closure of the incision, the suture 250 remains secured to the great toe and attached to the implant 100.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the invention.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention.

What is claimed is:

1. A method for correcting a bunion formed at a joint between a metatarsal and a great toe, the method comprising:
   selecting a target location on the metatarsal;
   creating an osteotomy in the metatarsal at the target location, the osteotomy resecting the metatarsal into a first metatarsal portion and a separate second metatarsal portion;
   implanting an implant into the metatarsal, the implant comprising a monolithic body having a head and an anchor, wherein implanting the implant into the metatarsal comprises inserting the anchor into the intramedullary canal of the first metatarsal portion;
   securing a length of suture to the great toe;
   tensioning the suture to re-align the great toe relative to the first metatarsal portion; and
   attaching the length of suture to the implant head.

2. The method of claim 1, further comprising inserting at least one k-wire into the metatarsal adjacent to the target location.

3. The method of claim 2, further comprising mounting a guide block onto the k-wire, wherein the guide block defines a cutting slot.

4. The method of claim 3, further comprising actuating a cutting tool through the cutting slot to create the osteotomy in the metatarsal.

5. The method of claim 4, wherein the cutting tool is selected from the group consisting of a broach, a saw, a blade, a chisel, an osteotome, a curette, a pick, and a rasp.

6. The method of claim 1, further comprising attaching the implant head to the second metatarsal portion.

7. The method of claim 1, wherein the incision is 0.5 inch or less in length.

8. A method for correcting a bunion formed at a joint between a metatarsal and a great toe, the method comprising:
   selecting a target location on the metatarsal;
   positioning a guide block at the target location;
   guiding a cutting instrument with the guide block to create an osteotomy in the metatarsal at the target location, the osteotomy dividing the metatarsal into a first metatarsal portion and a separate second metatarsal portion;
   implanting an implant into the metatarsal, the implant comprising a monolithic body having a head and an anchor, wherein implanting the implant into the metatarsal comprises inserting the anchor into the intramedullary canal of the first metatarsal portion;
   securing a length of suture to the great toe;
   tensioning the suture to re-align the great toe relative to the first metatarsal portion; and
   attaching the length of suture to the implant head.

9. The method of claim 8, further comprising inserting at least one k-wire into the metatarsal adjacent to the target location;
   mounting the guide block onto the k-wire, wherein the guide block defines a cutting slot; and
   actuating the cutting instrument through the cutting slot to create the osteotomy in the metatarsal.

10. The method of claim 8, wherein the cutting instrument is selected from the group consisting of a broach, a saw, a blade, a chisel, an osteotome, a curette, a pick, and a rasp.

11. The method of claim 8, wherein a joint capsule surrounds the joint, wherein securing the length of suture to the great toe comprises securing the length of suture to the joint capsule.

12. The method of claim 8, further comprising attaching the implant head to the second metatarsal portion.

13. The method of claim 8, wherein the incision is 0.5 inch or less in length.

14. A method for correcting a bunion formed at a joint between a metatarsal and a great toe, the method comprising:
- selecting a target location on the metatarsal;
- creating an osteotomy in the metatarsal at the target location, the osteotomy dividing the metatarsal into a first metatarsal portion and a separate second metatarsal portion;
- implanting an implant into the metatarsal, the implant comprising a monolithic body having a head and an anchor, wherein implanting the implant into the metatarsal comprises implanting the anchor into the first metatarsal portion;
- securing a length of suture to a joint capsule surrounding the joint;
- tensioning the length of suture to re-align the great toe relative to the first metatarsal portion;
- attaching the length of suture to the implant head; and
- fastening the implant head to the second metatarsal portion.

15. The method of claim 14, wherein the first metatarsal portion is proximal to the second metatarsal portion.

16. The method of claim 15, further comprising:
- translating the second metatarsal portion to expose a distal-facing surface of the first metatarsal portion; and
- inserting the implant anchor through the distal-facing surface into the intramedullary canal of the first metatarsal portion.

17. The method of claim 16, further comprising abutting the implant head against the distal-facing surface on the first metatarsal portion.

18. The method of claim 14, wherein the implant head further comprises a transverse bore, wherein attaching the length of suture to the implant head comprises passing the suture through the transverse bore.

19. The method of claim 14, comprising:
- making an incision along a side of the metatarsal before selecting the target location, creating the osteotomy, implanting the implant, securing the length of suture to the joint capsule, tensioning the length of suture, attaching the length of suture to the implant head, and fastening the implant head to the second metatarsal portion; and
- closing the incision after selecting the target location, creating the osteotomy, implanting the implant, securing the length of suture to the joint capsule, tensioning the length of suture, attaching the length of suture to the implant head, and fastening the implant head to the second metatarsal portion, wherein the suture is a non-resorbable suture, and wherein the length of suture remains secured to the joint capsule and attached to the implant after closing the incision.

* * * * *